United States Patent [19]

Levitt

[11] Patent Number: 4,569,995
[45] Date of Patent: Feb. 11, 1986

[54] SULFAMOYL CHLORIDES

[75] Inventor: George Levitt, Wilmington, Del.

[73] Assignee: E. I. Du Pont de Nemours and Company, Wilmington, Del.

[21] Appl. No.: 505,729

[22] Filed: Jun. 20, 1983

Related U.S. Application Data

[60] Division of Ser. No. 244,173, Mar. 25, 1981, Pat. No. 4,401,816, which is a continuation-in-part of Ser. No. 144,857, Apr. 29, 1980, abandoned.

[51] Int. Cl.$^4$ .................. C07D 251/16; C07D 251/46; C07D 251/22; C07D 403/12
[52] U.S. Cl. ..................................... 544/212; 544/213
[58] Field of Search ....................... 544/212, 194, 213; 71/93

[56] References Cited

U.S. PATENT DOCUMENTS 4,368,067  1/1983  Budzinski et al. .................. 544/212
4,448,959  5/1984  Bohner ................................ 544/213

OTHER PUBLICATIONS

Trueb et al., Chemical Abstracts, vol. 99, entry 105288x (1983).

*Primary Examiner*—John M. Ford

[57] ABSTRACT

Sulfamoyl chlorides are useful intermediates for the preparation of highly herbicidal end products.

11 Claims, No Drawings

SULFAMOYL CHLORIDES

RELATED APPLICATIONS

This application is a divisional application of my copending application U.S. Ser. No. 244,173, filed Mar. 25, 1981, now U.S. Pat. No. 4,401,816, which is a continuation-in-part of my application U.S. Ser. No. 144,857 which was filed Apr. 29, 1980, now abandoned.

BACKGROUND OF THE INVENTION

This invention relates to sulfamoyl chlorides which are useful as intermediates for preparing sufamides and pyrrole sulfonamides which are useful as agricultural chemicals and particularly as herbicides.

The sulfamides of this invention are compounds of the formula

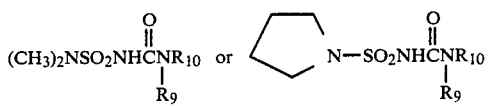

wherein $R_{10}$ and $R_9$ are as defined below.

The pyrrole compounds are disclosed in copending U.S. application Ser. No. 244,172, now U.S. Pat. No. 3,368,067, and have the general formulae

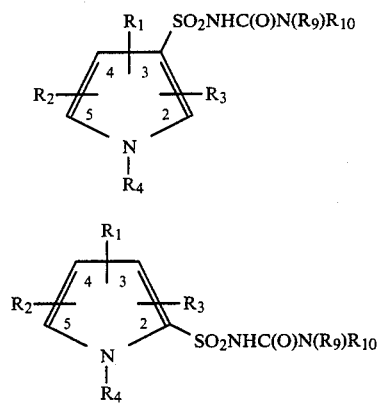

wherein
$R_1$ is H, $C_1-C_4$ alkyl, $NO_2$, CN, $C(O)CCl_3$, $SO_2R_{11}$, $C(O)R_5$, or $CO_2H$;
$R_2$ is H or $C_1-C_4$ alkyl;
$R_3$ is H, $C_1-C_4$ alkyl, Cl or Br;
$R_4$ is H, $C_1-C_4$ alkyl, cyanoethyl, $C_5-C_6$ cycloalkyl, benzyl, phenyl substituted with Cl or $NO_2$, or $C(O)R_6$;
$R_5$ is $C_1-C_4$ alkyl or $C_1-C_4$ alkoxy;
$R_6$ is $C_1-C_4$ alkyll, $C_1-C_4$ alkoxy, or $NR_7R_8$;
$R_7$ and $R_8$ are independently $C_1-C_2$ alkyl;
$R_9$ is H, $CH_3$ or $OCH_3$;
$R_{11}$ is $C_1-C_4$ alkyl;
$R_{10}$ is

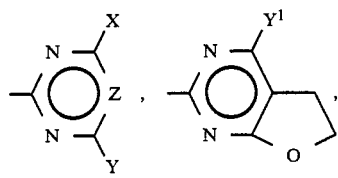

X is $CH_3$ or $OCH_3$;
Y is H, $CH_3$, $OCH_3$, $OCH_2CH_3$, $OCH_2CF_3$, Cl, $CH_2OCH_3$, $CH_2OCH_2CH_3$ or $CF_3$;
$Y^1$ is H, $CH_3$, $OCH_3$, Cl or $OCH_2CH_3$; and
Z is CH, N, $CCH_3$ $CCH_2CH_3$, $CCH_2CH_2Cl$, CCl, CBr or Cf;
and their agriculturally suitable salts; provided that
(1) when $R_4$ is $C(O)R_6$, t-butyl or phenyl substituted with Cl or $NO_2$, then $R_1$ is H or $C_1-C_4$ alkyl and $R_1$, $R_2$ and $R_3$ cannot be s-butyl or isopropyl;
(2) $R_1$, $R_2$, $R_3$ and $R_{11}$ cannot be t-butyl;
(3) in Formula Ia, when $R_1$ is $NO_2$, then $R_1$ cannot be in the 5-position;
(4) in Formula Ia, when $R_1$ is not in the 5-position, $R_2$ and $R_3$ are other than H, and $R_1$ must be other than H unless both $R_2$ and $R_3$ are H;
(5) in Formula Ia, $R_3$ cannot be Cl or Br;
(6) in Formula Ib, $R_1$ cannot be $C(O)CCl_3$; and
(7) in Formula Ib, when $R_3$ is Cl or Br, then $R_3$ is in the 3-position and $R_1$ is in the 5-position and $R_1$ cannot be H or $C_1-C_4$ alkyl.

The presence of undesired vegetation causes substantial damage to useful crops, especially agricultural products that satisfy man's basic food and fiber needs such as soybeans, barley, wheat and the like. The current population explosion and concomitant world food shortage demand improvements in the efficiency of producing these crops. Prevention or minimizing the loss of a portion of such crops by killing or inhibiting the growth of undesired vegetation, with herbicidal compounds such as those described above, is one way of improving this efficiency.

Useful intermediates, such as those of the instant invention, facilitate the production of the desired herbicidal compounds.

German Pat. No. 2,439,087 discloses the following compound:

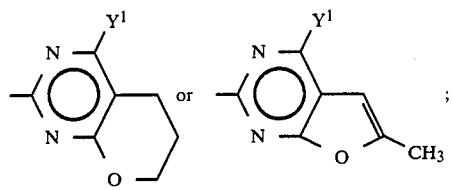

SUMMARY OF THE INVENTION

This invention relates to sulfamoyl chlorides of Formula I which are useful as intermediates for preparing sulfamides and pyrrole sulfonamides which are useful as agricultural chemicals and particularly as herbicides.

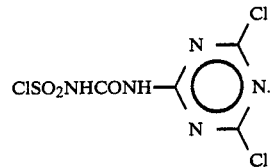

wherein $R_9$ is H, CH$_3$ or OCH$_3$;
$R^1$ is Cl, (CH$_3$)$_2$N or

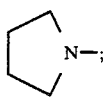

$R_{10}$ is

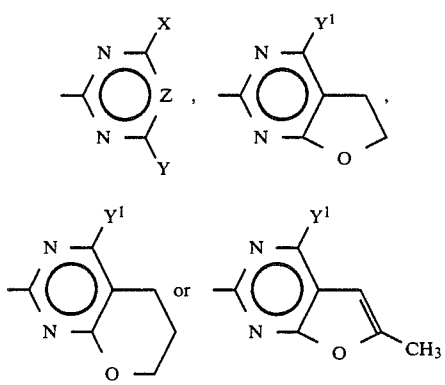

X is CH$_3$ or OCH$_3$;
Y is H, CH$_3$, OCH$_3$, OCH$_2$CH$_3$, OCH$_2$CF$_3$, Cl, CH$_2$OCH$_3$, CH$_2$OCH$_2$CH$_3$ or CF$_3$;
Y$^1$ is H, CH$_3$, OCH$_3$, Cl or OCH$_2$CG$_3$;
Z is CH, N, CCH$_3$ CCH$_2$CH$_3$, CCH$_2$CH$_2$Cl, CCl, CBr or CCF$_3$.

PREFERRED COMPOUNDS

Preferred intermediates for reasons of higher activity of the derived herbicides are:
(1) Compounds of the generic scope wherein $R_9$ is H or CH$_3$ and $R^1$ is Cl;
(2) Compounds of Preferred (1) wherein Y is CH$_3$, OCH$_3$ or OCH$_2$CH$_3$; and Z is CH or N;
(3) Compounds of Preferred (2) wherein Y$^1$ is H, CH$_3$ or OCH$_3$;
(4) Compounds of Preferred (1)-(3) wherein $R_9$ is H; and
(5) Compounds of Preferred (4) wherein $R_{10}$ is 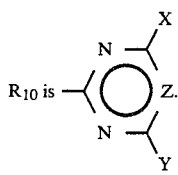

Specifically preferred for reasons of greatest activity of the resulting herbicides are:
[(4,6-dimethylpyrimidin-2-yl)aminocarbonyl]sulfamoyl chloride;
[(4-methoxy-6-methylpyrimidin-2-yl)aminocarbonyl]sulfamoyl chloride;
[(4,6-dimethoxypyrimidin-2-yl)aminocarbonyl]sulfamoyl chloride;
[(4,6-dimethyl-1,3,5-triazin-2-yl)aminocarbonyl]-sulfamoyl chloride;
[(4-methoxy-6-methyl-1,3,5-trazin-2-yl)aminocarbonyl]-sulfamoyl chloride;
[(4,6-dimethoxy-1,3,5-triazin-2-yl)aminocarbonyl]-sulfamoyl chloride;
[(4-ethoxy-6-methyl-1,3,5-triazin-2-yl)aminocarbonyl]-sulfamoyl chloride;
[(5,6-dihydro-4-methylfuro[2,3-d]pyrimidin-2-yl)-aminocarbonyl]sulfamoyl chloride;
[(5,6-dihydrofuro[2,3-d]pyrimidin-2-yl)aminocarbonyl]-sulfamoyl chloride;
[(5,6-dihydro-4-methoxy[2,3-d]pyrimidin-2-yl)aminocarbonyl]sulfamoyl chloride;
N-[(4,6-dimethyl-2-pyrimidinyl)aminocarbonyl]-1-pyrrolidinesulfonamide;
N-[(dimethylamino)sulfonyl]-N'-(4,6-dimethyl-2-pyrimidinyl)urea;
[(4,6-dimethylfuro[2,3-d]pyrimidin-2-yl)aminocarbonyl]-sulfamoyl chloride;
[(4,6-dimethylpyrimidin-2-yl)(methyl)aminocarbonyl]-sulfamoyl chloride;
[(4,6-dimethoxypyrimidin-2-yl)(methyl)aminocarbonyl]-sulfamoyl chloride;
[(4-methoxy-6-methylpyrimidin-2-yl)(methyl)aminocarbonyl]sulfamoyl chloride;
[(4,6-dimethyl-1,3,5-triazin-2-yl)(methyl)aminocarbonyl]-sulfamoyl chloride;
[(4,6-dimethoxy-1,3,5-triazin-2-yl)(methyl)aminocarbonyl]-sulfamoyl chloride; and
[(4-methoxy-6-methyl-1,3,5-triazin-2-yl)(methyl)aminocarbonyl]sulfamoyl chloride.

DETAILED DESCRIPTION OF THE INVENTION

The compounds of this invention can be prepared according to the process of Equation 1.

Equation 1

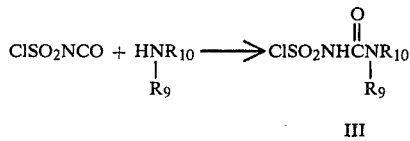

wherein $R_9$ and $R_{10}$ are as previously defined.

The intermediates are then reacted with an appropriate nucleophile such as dimethylamine as shown in Equation 2 to prepare the herbicidal compounds Ic.

Equation 2

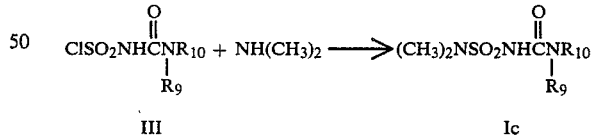

The reaction of Equation 1 is best carried out by suspending the heterocyclicamine,

in an inert aprotic solvent such as tetrahydrofuran at −80° to −40° C., methylene chloride or nitroethane at −80° to 0° C., or nitromethane at −10° to 10° C. One equivalent of chlorosulfonyl isocyanate is then added at a rate such that the exothermic reaction can be moderated within the temperature limits for the desired reaction. The reaction is generally completed within one hour. The sulfamoyl chlorides of Formula III of this invention are not isolated but are treated with the appropriate nucleophilic reagent to form the desired herbicidal compounds.

One such product is obtained by the reaction of dimethylamine with [(4,6-dimethylpyrimidin-2-yl)-aminocarbonyl]sulfamoyl chloride as described above in Equation 2 and subsequently in Example 1. In this preparation, the sulfamoyl chloride containing solution is treated with an excess of aqueous dimethylamine at ambient temperature. After stirring the reaction mixture overnight at ambient temperature, the product is isolated from the methylene chloride reaction solvent following aqueous extraction of the reaction by-products.

The sulfamoyl chlorides of Formula III also react with pyrroles II as shown in Equations 3 and 3A to form novel herbicidal compounds (Ia and Ib) as described above in the Background of the Invention, the pyrroles of copending U.S. application Ser. No. 244,172 now U.S. Pat. No. 3,368,067.

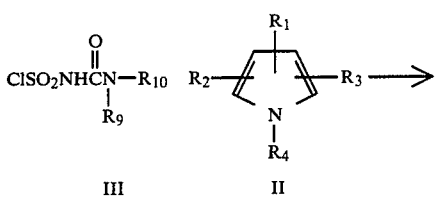

Equation 3

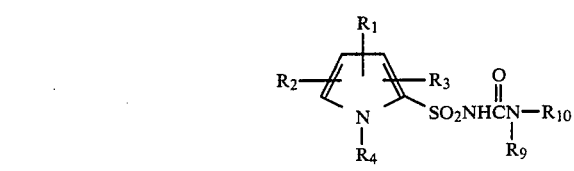

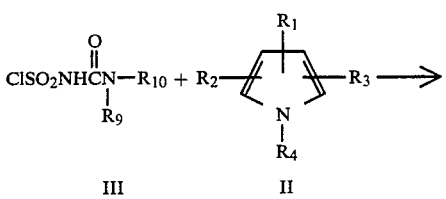

Equation 3A

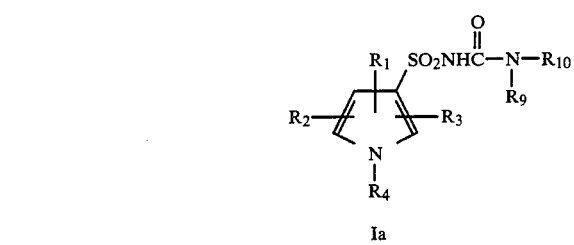

The process of Equations 3 and 3A is useful for preparing compounds of Formulae Ia and Ib where
  $R_1$ is H, $C_1$–$C_4$ alkyl, $NO_2$, CN, $C(O)CCl_3$, $SO_2R_{11}$, $C(O)R_5$, or $CO_2H$;
  $R_2$ is H or $C_1$–$C_4$;
  $R_3$ is H, $C_1$–$C_4$ alkyl, Cl or Br;
  $R_4$ is H, $C_1$–$C_4$ alkyl, cyanoethyl, $C_5$–$C_6$ cycloalkyl, benzyl, phenyl substituted with Cl or $NO_2$, or $C(O)R_8$;
  $R_5$ is $C_1$–$C_4$ alkyl or $C_1$–$C_4$ alkoxy;
  $R_6$ is $C_1$–$C_4$ alkyl, $C_1$–$C_4$ alkoxy, or $NR_7R_8$;
  $R_7$ and $R_8$ are independently $C_1$–$C_2$ alkyl; and
  $R_{11}$ is $C_1$–$C_4$ alkyl;
provided that
  (1) when $R_4$ is $C(O)R_6$, t-butyl or phenyl substituted with Cl or $NO_2$, then $R_1$ is H or $C_1$–$C_4$ alkyl and $R_1$, $R_2$ and $R_3$ cannot be sec-butyl or isopropyl;
  (2) $R_1$, $R_2$, $R_3$ and $R_{11}$ cannot be t-butyl;
  (3) in Formula Ia, when $R_1$ is $NO_2$, then $R_1$ cannot be in the 5-position;
  (4) in Formula Ia, when $R_1$ is not in the 5-position, $R_2$ and $R_3$ are other than H, and $R_1$ must be other than H unless both $R_2$ and $R_3$ are H;
  (5) in Formula Ia, $R_3$ cannot be Cl or Br;
  (6) in Formula Ib, $R_1$ cannot be $C(O)CCl_3$; and
  (7) in Formula Ib, when $R_3$ is Cl or Br, then $R_3$ is in the 3-position and $R_1$ is in the 5-position and $R_1$ cannot be H or $C_1$–$C_4$ alkyl.

Intermediate III is not ordinarily isolated but is contacted with from one to ten equivalents of the appropriately substituted pyrrole of Formula II in a solution which may also contain a Friedel-Crafts catalyst such as aluminum (III) chloride, aluminum (III) bromide, gallium (III) chloride, tin (IV) chloride, iron (III) chloride, zinc (II) chloride, antimony (V) fluoride, antimony (III) chloride, antimony (V) chloride, titanium (IV) chloride, boron (III) fluoride, sulfuric acid or hydrofluoric acid. The reaction mixture is preferably maintained at a temperature of $-80°$ to $0°$ C. for a period of 1 to 4 hours, followed by a period of 16 to 48 hours at $25°$ to $40°$ C.

The products of Formula Ia or Ib may be isolated by partitioning the reaction mixture between dilute aqueous alkali and an organic solvent such as dichloromethane or diethyl ether. The products are soluble in the aqueous phase and may be precipitated by the addition of excess acid, preferably glacial acetic acid.

In some instance, isomeric products are obtained and these materials may often be separated by column chromatography, preparative high pressure or medium pressure liquid chromatography or similar methods.

General Synthesis

The synthesis of heterocyclic amine derivatives has been reviewed in "The Chemistry of Heterocyclic Compounds," a series published by Interscience Publ., New York and London. Aminopyrimidines are described by D. J. Brown in "The Pyrimidines", Vol. XVI of the above series. The preparation of furo[2,3-d]pyrimidines and cyclopentanopyrimidines has been described in U.S. Patent Application 109,262, filed Jan. 18, 1980.

2-Amino-1,3,5-triazines can be synthesized according to methods described in E. M. Smolin and L. Rapoport in "s-Triazines and Derivatives," Vol. XIII of the same series. 2-Amino-1,3,5-triazines are also conveniently prepared by the methods of K. R. Huffman and F. C. Schaefer in *J. Org. Chem.*, 28, 1812–1815 and 1816–1821 (1963).

The synthesis of the bicyclic heterocyclic amines VIII and IX wherein $Y^1$ is as previously defined is described in the unexamined European Pat. No. 15-683, published Sept. 17, 1980.

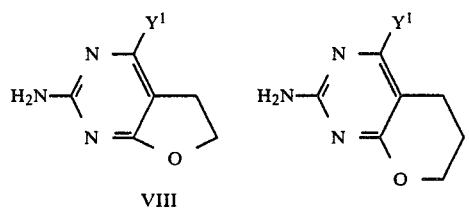

VIII    IX

The pyrimidine intermediates of structure X in which $Y^1$ is methyl have been reported in the literature by E. Bisagni, et. al. *Bull. Soc. Chem. Fr.* 803 (1969). A more efficient procedure is depicted in the equation below.

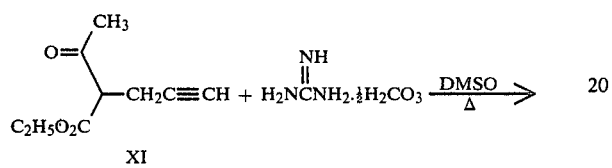

XI

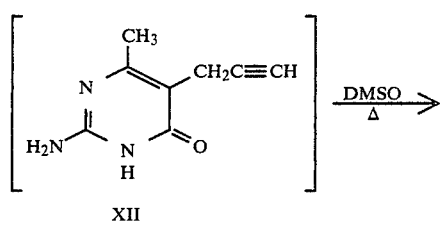

XII

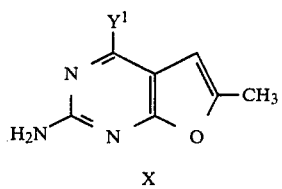

X

The known keto-esters precursor XI (e.g., J. R. Tinker and T. E. Whatmough, *J. Amer. Chem. Soc.*, 74, 5235 (1952)) is contacted with excess guanidine carbonate in an organic solvent, preferably a polar aprotic solvent such as dimethylsulfoxide (DMSO), dimethylformamide (DMF) or N,N-dimethylacetamide, at a temperature of 80° to 200°, preferably 100° to 160°, ambient pressure and preferably under an inert atmosphere to yield both XII and X (where $Y^1$ is $CH_3$). The products are isolated upon dilution of the reaction mixture with, for example, acetone and water successively. Higher reaction temperatures and longer reaction times (e.g., in DMSO at 130°–160° for 2 to 8 hours) favor the production of X over XII.

The pyrimidine intermediates X in which $Y^1$ is Cl may be prepared by condensing the known ethyl 2-carboethoxy-4-pentynoate XIII with guanidine carbonate in an alcohol solvent such as ethanol to give the intermediate pyrimidine XIV as shown below.

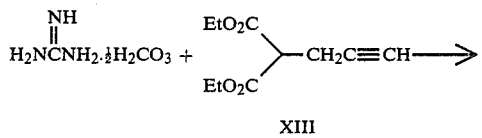

XIII

-continued

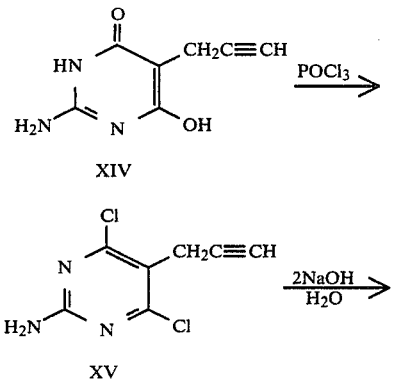

XIV

XV

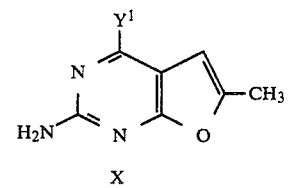

X

Conversion to the dichloropyrimidine XV may be accomplished by heating XIV in phosphorous oxychloride. The product may be isolated by removal of the phosphorous oxychloride under reduced pressure, trituration of the residue with ice-water and filtration of the solid product. Contacting the dichloropyrimidine with two equivalents of an aqueous alkali metal hydroxide, such as sodium hydroxide yields the furopyrimidine X in which $Y^1$ is Cl. The reaction is best carried out in the presence of a solubilizing agent which is water miscible, such as t-butanol, dioxane or tetrahydrofuran, and at temperatures of 20° to 100° or conveniently at the boiling point of the solvent mixture used. The product may be isolated by cooling the mixture or further dilution with water to effect precipitation.

Compounds of formula X in which $Y^1$ is $OCH_3$ or $OCH_2CH_3$ may be prepared by contacting the corresponding compound in which $Y^1$ is Cl with sodium methoxide in boiling methanol or with sodium ethoxide in refluxing ethanol, respectively. The product is obtained on evaporation of the alcohol solution, trituration of the residue with cold water and subsequent filtration.

Compounds of formula X in which $Y^1$ is H may be prepared by reaction of the corresponding compound in which $Y^1$ is Cl with a reducing agent such as zinc dust in acetic acid or p-toluenesulfonylhydrazide the latter by a procedure similar to that described by Albert and Royer, *J. Chem. Soc.*, 1148 (1949).

The aminoheterocyclic intermediates $R_{11}R_{12}NH$ in which $R_{11}$ is $CH_3$, may be prepared by the following procedure, or by obvious modifications thereof.

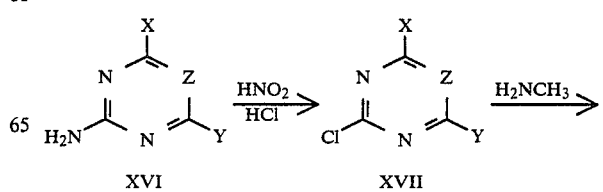

XVI    XVII

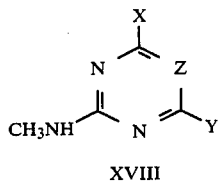

A solution of the amine XVI in concentrated hydrochloric acid is contacted with an aqueous sodium nitrite solution and the chloro compound XVII is isolated by filtration of the acidic solution (see for example, Bee and Rose, *J. Chem. Soc. C.,* 2051 (1966) for the case in which Z is CH and X and Y are $OCH_3$). Displacement of the chlorine may be accomplished by heating with an excess of methylamine in water to obtain the methylaminoheterocycle XVIII.

N-Methoxyamino heterocycles can be prepared by procedures reported on the literature [see, for example, Belgian Pat. No. 618,563 and J. T. Shaw, et al. *J. Org. Chem.,* 27 4054 (1962)] and the procedure illustrated below.

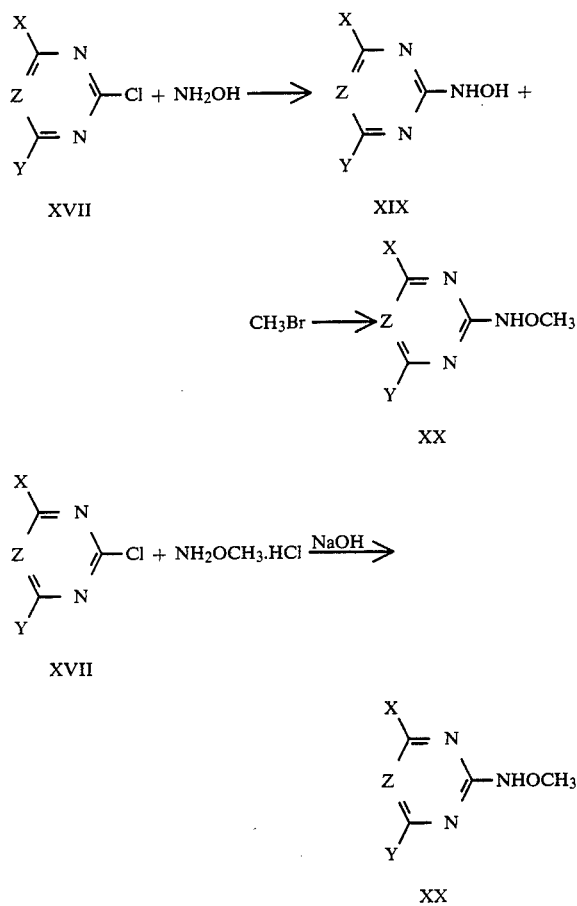

Chloro compound XVII is reacted with hydroxylamine to form derivative XIX which may be alkylated with methyl bromide to afford the N-methoxy heterocyclic amine XX. This compound may alternately be prepared in one step by treatment of XVII and O-methyl hydroxylamine hydrochloride with an alkali metal hydroxide such as sodium hydroxide.

The synthesis of pyrroles has been reviewed, e.g., by R. Alan Jones and G. P. Bean, "The Chemistry of Pyrroles," Academic Press, London (1977) and by J. M. Patterson, *Synthesis,* 281–304 (1976). These articles are herein incorporated by reference. The preparation of a wide variety of alkyl substituted pyrroles is reported in the literature and would be known to one skilled in the art.

The preparation of 2-halopyrroles is described in *J. Org. Chem.,* 40, 3161–69 (1975) and the methods taught and referenced therein may be readily applied by one skilled in the art to the preparation of 2-halopyrroles III and V in which $R_1$ is Cl or Br.

The compounds of this invention and their use as intermediates are further illustrated by the following examples. In the following examples all temperatures are in °C and parts are by weight unless otherwise indicated.

EXAMPLE 1

[(4,6-Dimethylpyrimidin-2-yl)aminocarbonyl]sulfamoyl chloride and N'-[(4,6-dimethylpyrimidin-2-yl)aminocarbonyl]-N,N-dimethylsulfamide To 2.5 g of 2-amino-4,6-dimethylpyrimidine in 30 ml of methylene chloride at 0° was added 2.8 g of chlorosulfonyl isocyanate dropwise with stirring. The resultant mixture containing [(4,6-dimethylpyrimidin-2-yl)aminocarbonyl]sulfamoyl chloride was allowed to come to room temperature and then 7.2 g of 25% aqueous dimethylamine was added dropwise with stirring and cooling. The mixture was stirred overnight at ambient temperature, mixed with 2 volumes of ice-water and enough methylene chloride was added to dissolve most of the remaining solid. The methylene chloride phase was separated, washed twice with water, dried over magnesium sulfate, filtered and evaporated in-vacuo to yield the desired sulfamide derivative melting at 183°–185° C. It showed absorption peaks by infrared spectroscopy at 1700, 1620 and 1550 $cm^{-1}$ and Nuclear Resonance Spectroscopy (60 MC) at 2.45 δ(singlet), 3.02 δ(singlet) and 6.8 δ(singlet) with integration ratios of 6:6:1. Both spectra are consistent for the proposed structure.

EXAMPLE 2

N-[(4,6-Dimethylpyrimidin-2-yl)aminocarbonyl]-1-pyrrolidinesulfonamide

To a methylene chloride solution of [(4,6-dimethylpyrimidin-2-yl)aminocarbonylsulfamoyl chloride, prepared as in Example 1, was added dropwise 2.9 ; g of pyrrolidine while maintaining the temperature at 20° C. The mixture was stirrred for 16 hours and added to 50 ml of ice-water. Enough methylene chloride was added to dissolve the solids present and the methylene chloride solution was washed twice with equal volumes of water, dried over magnesium sulfate, filtered and evaporated in-vacuo. The residue, m.p. 180° ∝ 181° C., showed absorption peaks by infrared spectroscopy at 1690, 1605 and 1550 $cm^{-1}$ and Nuclear Resonance Spectroscopy (60MC) at 2.02 δ(mult.) and 3.64 δ(mult.) for the pyrrolidine hydrogens, 2.6 δ(singlet) for $CH_3$ and 6.85 δpyrimidine H with integration ratios of 4:4:6:1, consistent for the desired structure.

EXAMPLE 3

[(4,6-Dimethylpyrimidin-2-yl)aminocarbonyl]sulfamoyl chloride and 2,5-dimethyl-N-[(4,6-dimethylpyrimidin-2-yl)aminocarbonyl]-1H-pyrrole-3-sulfonamide To a mechanically stirred suspension of 12.3 g (0.1 mole) of 2-amino-4,6-dimethylpyrimidine in 200 ml of dry dichloromethane maintained at 0° to 5° under a nitrogen atmosphere was added dropwise over 30 minutes a solution of 9.2 ml (0.1 mole) of chlorosulfonylisocyanate in 50 ml of ice-cold dichloromethane. After 30 minutes at 0° to 5°, the resulting yellow solution was treated dropwise over 15 minutes with 20 ml (0.197 mole) of 2,5-dimethylpyrrole. This mixture was stirred 30 minutes at 0° to 5° and allowed to stand overnight at room temperature.

The dichloromethane solution was decanted and the resulting reddish solid dissolved in a mixture of 50 ml methanol and 600 ml of 1N sodium hydroxide solution, acidified with 10% HCl and extracted with 4 portions of ethyl acetate. The ethyl acetate was evaporated in-vacuo to afford a brown solid which was dissolved in 50 ml methanol and 300 ml of dilute NaOH solution. The aqueous solution was washed with 2 portions of $CH_2Cl_2$, acidified with glacial acetic acid and extracted with 2 portions of $CH_2Cl_2$. The latter $CH_2Cl_2$ solutions were evaporated to afford the crude product which was purified by fractional crystallization from 20% acetone in $CH_2Cl_2$ to afford a white solid, m.p. 220°–222°. Mass spectral analysis showed m/e 123,

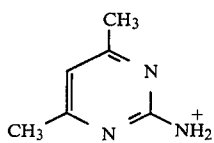

and m/e 200,

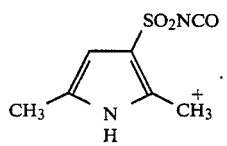

Anal. Calcd. for $C_{13}H_{17}N_5O_3S$: C, 48.3; H, 5.3 N, 21.7; S, 9.9; Found: C, 48.4; H, 5.4; N, 22.0; S, 9.8.

EXAMPLE 4

[(4,6-Dimethyl-1,3,5-triazin-2-yl)aminocarbonyl]sulfamoyl chloride

To a stirred suspension of 2-amino-4,6-dimethyl-1,3,5-triazine in 10 parts by volume of nitroethane at −10° to 0° is added dropwise an equivalent amount of chlorosulfonyl isocyanate. The mixture is stirred for one hour at −10° allowing for completion of the reaction to form [(4,6-dimethyl-1,3,5-triazin-2-yl)aminocarbonylsulfamoyl chloride. The additional reagent such as pyrrole is then added and the preparation of the stable herbicidal compound is continued as described in Example 2 or for Equations 3 and 3A.

By using methods described generally above and illustrated in Examples 1 and 3, compounds as shown in the following tables can similarly be prepared. These tables are not meant to be all inclusive but only illustrative of the breadth of the invention.

TABLE I

| $R_9$ | X | Y | Z |
|---|---|---|---|
| H | $CH_3$ | $OCH_3$ | CH |
| H | $OCH_3$ | $OCH_3$ | CH |
| H | $CH_3$ | $OC_2H_5$ | CH |
| H | $CH_3$ | Cl | CH |
| H | $CH_3$ | H | CH |
| H | $CH_3$ | $OCH_2CF_3$ | CH |
| H | $CH_3$ | $CH_2OCH_3$ | CH |
| H | $OCH_3$ | $CH_2OCH_3$ | CH |
| H | $OCH_3$ | $CH_2OC_2H_5$ | CH |
| H | $CH_3$ | $CF_3$ | CH |
| H | $OCH_3$ | $CF_3$ | CH |
| H | $CH_3$ | $CH_2OC_2H_5$ | CH |
| $CH_3$ | $OCH_3$ | $CH_3$ | CH |
| $CH_3$ | $OCH_3$ | $OCH_3$ | CH |
| $CH_3$ | $OCH_3$ | $OC_2H_5$ | CH |
| H | $OCH_3$ | Cl | CH |
| H | $OCH_3$ | $CH_2OCH_3$ | CH |
| H | $OCH_3$ | $OCH_2CF_3$ | CH |
| H | $CH_3$ | $CH_3$ | CCl |
| H | $CH_3$ | $OCH_3$ | CCl |
| H | $OCH_3$ | $OCH_3$ | CCl |
| H | $CH_3$ | $CH_3$ | $CCH_3$ |
| H | $CH_3$ | H | $CCH_3$ |
| H | $OCH_3$ | H | $CCH_3$ |
| H | $CH_3$ | H | CCl |
| H | $CH_3$ | $CH_3$ | CF |
| H | $CH_3$ | $CH_3O$ | CF |
| H | $CH_3$ | $CH_3$ | CBr |
| H | $CH_3$ | H | CBr |
| H | $CH_3$ | H | $CCH_2CH_3$ |
| H | $CH_3$ | H | $CCH_2CH_2Cl$ |
| H | $CH_3$ | $CH_3$ | $CCH_2CH_2Cl$ |
| H | $CH_3$ | H | CF |
| H | $OCH_3$ | H | CH |
| H | $OCH_3$ | Cl | CH |
| $CH_3$ | $CH_3$ | $CH_3$ | CH |
| $OCH_3$ | $CH_3$ | $CH_3$ | CH |
| $OCH_3$ | $CH_3$ | $OCH_3$ | CH |
| $OCH_3$ | $OCH_3$ | $OCH_3$ | CH |

TABLE Ia

| $R_9$ | X | Y |
|---|---|---|
| H | $CH_3$ | $CH_3$ |
| H | $CH_3$ | $OCH_3$ |
| H | $OCH_3$ | $OCH_3$ |
| H | $CH_3$ | $OCH_2CH_3$ |
| H | $CH_3$ | Cl |
| H | $CH_3$ | H |
| H | $CH_3$ | $OCH_2CF_3$ |
| H | $CH_3$ | $CH_2OCH_3$ |
| H | $OCH_3$ | $CH_2OCH_3$ |
| H | $OCH_3$ | $CH_2OCH_2CH_3$ |
| H | $CH_3$ | $CF_3$ |
| H | $OCH_3$ | $CF_3$ |
| H | $CH_3$ | $CH_2OC_2H_5$ |
| $CH_3$ | $OCH_3$ | $CH_3$ |
| $CH_3$ | $OCH_3$ | $OCH_3$ |
| $CH_3$ | $OCH_3$ | $OC_2H_5$ |

TABLE Ia-continued

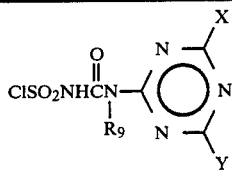

| R9 | X | Y |
|---|---|---|
| H | OCH3 | Cl |
| H | OCH3 | OCH2CF3 |
| OCH3 | CH3 | CH3 |
| OCH3 | OCH3 | CH3 |
| OCH3 | OCH3 | OCH3 |
| OCH3 | CH3 | OCH2CH3 |
| OCH3 | CH3 | OCH2CF3 |
| OCH3 | CH3 | CH2OCH3 |
| OCH3 | CH3 | OCH2CF3 |
| CH3 | CH3 | CH3 |

TABLE Ib

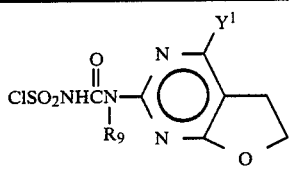

| R9 | Y1 |
|---|---|
| H | H |
| H | OCH3 |
| H | CH3 |
| H | Cl |
| H | OCH2CH3 |
| OCH3 | OCH3 |
| OCH3 | CH3 |
| OCH3 | Cl |
| OCH3 | OC2H5 |
| OCH3 | H |
| CH3 | CH3 |
| CH3 | OCH3 |
| CH3 | OCH2CH3 |
| CH3 | Cl |
| CH3 | H |

TABLE Ic

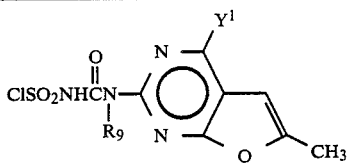

| R9 | Y1 |
|---|---|
| H | CH3 |
| H | OCH3 |
| CH3 | CH3 |
| CH3 | OCH3 |
| OCH3 | CH3 |
| OCH3 | OCH3 |
| H | H |
| CH3 | H |
| OCH3 | H |
| H | Cl |
| CH3 | Cl |
| OCH3 | Cl |
| H | OCH2CH3 |
| CH3 | OCH2CH3 |
| OCH3 | OCH2CH3 |

TABLE Id

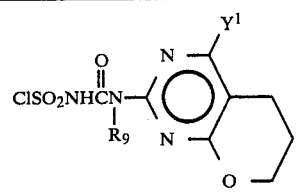

| R9 | Y1 |
|---|---|
| H | CH3 |
| H | OCH3 |
| CH3 | CH3 |
| CH3 | OCH3 |
| OCH3 | CH3 |
| OCH3 | OCH3 |
| H | H |
| CH3 | H |
| OCH3 | H |
| H | Cl |
| CH3 | Cl |
| OCH3 | Cl |
| H | OCH2CH3 |
| CH3 | OCH2CH3 |
| OCH3 | OCH2CH3 |

UTILITY

Test Procedure A

Seeds of crabgrass (*Digitaria spp.*), barnyardgrass (*Echinochloa crusgalli*), wild oats (*Avena fatua*), *Cassia tora*, morningglory (*Ipomoea spp.*), cocklebur (*Xanthium spp.*), sorghum, corn, soybean, rice, wheat and nutsedge tubers were planted in a growth medium and treated pre-emergence with the chemicals dissolved in a non-phytotoxic solvent. At the same time, cotton having five leaves (including cotyledonary ones), bush-beans with the third trifoliate leaf expanding, crab-grass with two leaves, barnyardgrass with two leaves, wild oats with one leaf, cassia with three leaves (including cotyledonary ones), morningglory with four leaves (including the cotyledonary ones), cocklebur with four leaves )including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment. Ratings for compounds tested by this procedure are recorded in Table A.

0=no effect;
10=complete control;
C=chlorosis/necrosis;
G=growth retardation;
H=nominal response;
6F=delayed flowering; and
6Y—abscised buds or flowers.

It is obvious from the data that this compound has herbicidal activity in plants. The compound represents an end-product produced from an intermediate of this invention.

TABLE A
PLANT RESPONSE

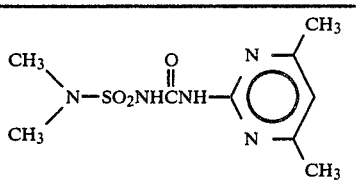

| kg/ha | 2 |
|---|---|
| POST-EMERGENCE | |
| BUSHBEAN | 2C, 7G, 6Y |
| COTTON | 2C, 5G |
| MORNINGGLORY | 1C |
| COCKLEBUR | 2G, 6F |
| CASSIA | 0 |
| NUTSEDGE | 0 |
| CRABGRASS | 1H |
| BARNYARDGRASS | 1C |
| WILD OATS | 0 |
| WHEAT | 0 |
| CORN | 3G |
| SOYBEAN | 1H, 4G |
| RICE | 1C, 8G |
| SORGHUM | 1C, 4G |
| PRE-EMERGENCE | |
| MORNINGGLORY | 0 |
| COCKLEBUR | 6G |
| CASSIA | 5G |
| NUTSEDGE | 4G |
| CRABGRASS | 0 |
| BARNYARDGRASS | 0 |
| WILD OATS | 0 |
| WHEAT | 0 |
| CORN | 3G |
| SOYBEAN | 1C |
| RICE | 4G |
| SORGHUM | 0 |

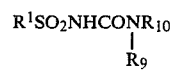

| kg/ha | 2 | 2 |
|---|---|---|
| POST-EMERGENCE | | |
| BUSHBEAN | 0 | 2C, 5G, 6Y |
| COTTON | 0 | 1C |
| MORNINGGLORY | 0 | 0 |
| COCKLEBUR | 0 | 1C |
| CASSIA | 0 | 0 |
| NUTSEDGE | 0 | 0 |
| CRABGRASS | 0 | 0 |
| BARNYARDGRASS | 0 | 0 |
| WILD OATS | 0 | 0 |
| WHEAT | 0 | 0 |
| CORN | 0 | 2C, 5H |
| SOYBEAN | 0 | 1C, 3H |
| RICE | 0 | 0 |
| SORGHUM | 0 | 2C |
| PRE-EMERGENCE | | |
| MORNINGGLORY | 0 | 8G |
| COCKLEBUR | 0 | — |
| CASSIA | 0 | 8G |
| NUTSEDGE | 0 | 0 |
| CRABGRASS | 0 | 0 |
| BARNYARDGRASS | 0 | 5G |
| WILD OATS | 0 | 0 |
| WHEAT | 0 | 0 |
| CORN | 0 | 4G |
| SOYBEAN | 0 | 0 |
| RICE | 0 | 3G |
| SORGHUM | 0 | 4G |

The data for N-[(4,6-dimethylpyrimidin-2-yl)aminocarbonyl]-1-pyrrolidinesulfonamide show two tests on different samples of the same compound. The failure to show activity in one test may have resulted from difficulty in formulating (dissolving) the compound in the test solution.

What is claimed is:

1. A compound selected from $$R^1SO_2NHCONR_{10} \quad (I)$$
$$\quad | \quad$$
$$\quad R_9$$

wherein
$R_9$ is H, $CH_3$ or $OCH_3$;
$R^1$ is Cl, $(CH_3)_2N$ or

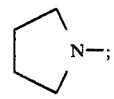

$R_{10}$ is

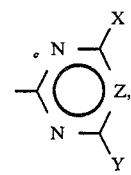

X is $CH_3$ or $OCH_3$;
Y is H, $CH_3$, $OCH_3$, $OCH_2CH_3$, $OCH_2CF_3$, Cl, $CH_2OCH_3$, $CH_2OCH_2CH_3$ or $CF_3$; and
Z is N.

2. A compound of claim 1 wherein $R_9$ is H or $CH_3$, and $R^1$ is Cl.
3. A compound of claim 1 wherein $R^1$ is Cl.
4. A compound of claim 1 wherein $R^1$ is $(CH_3)_2N-$ or

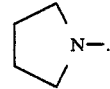

5. A compound of claim 1 wherein $R_9$ is H.
6. A compound of claim 2 wherein Y is $CH_3$, $OCH_3$ or $OCH_2CH_3$.
7. A compound of claim 6 wherein $Y^1$ is H, $CH_3$ or $OCH_3$.
8. A compound of claim 1 [(4,6-dimethyl-1,3,5-triazin-2-yl)aminocarbonyl]-sulfamoyl chloride.
9. A compound of claim 1 [(4-methoxy-6-methyl-1,3,5-triazin-2-yl)aminocarbonyl]-sulfamoyl chloride.
10. A compound of claim 1 [(4,6-dimethoxy-1,3,5-triazin-2-yl)aminocarbonyl]-sulfamoyl chloride.
11. A compound of claim 1 [(4-ethoxy-6-methyl-1,3,5-triazin-2-yl)aminocarbonyl]-sulfamoyl chloride.

* * * * *